United States Patent [19]

Vora

[11] Patent Number: 4,523,045
[45] Date of Patent: Jun. 11, 1985

[54] PROCESS FOR CONVERTING PARAFFINS TO OLEFINS

[75] Inventor: Bipin V. Vora, Elk Grove Village, Ill.

[73] Assignee: UOP Inc., Des Plaines, Ill.

[21] Appl. No.: 637,234

[22] Filed: Aug. 2, 1984

Related U.S. Application Data

[63] Continuation-in-part of Ser. No. 596,867, Apr. 4, 1984.

[51] Int. Cl.³ .............................................. C07C 5/00
[52] U.S. Cl. .................................... 585/254; 585/252; 585/654; 585/315; 585/324; 585/259; 585/262
[58] Field of Search ............... 585/254, 654, 252, 315, 585/324, 259, 262

[56] References Cited

U.S. PATENT DOCUMENTS

| 3,234,298 | 2/1966 | van Zigil Langhout et al. | 585/274 |
|---|---|---|---|
| 3,239,455 | 3/1966 | Lickus et al. | 208/212 |
| 3,472,763 | 10/1969 | Cosyns et al. | 208/255 |
| 3,484,498 | 12/1969 | Berg | 585/323 |
| 3,617,504 | 11/1971 | Berg | 208/100 |
| 3,655,621 | 4/1972 | Kasperik et al. | 585/262 |
| 3,662,015 | 5/1972 | Komatsu et al. | 585/261 |
| 3,696,160 | 10/1972 | Chomyn | 585/262 |
| 4,133,842 | 6/1979 | Anderson | 260/683.3 |
| 4,409,401 | 10/1983 | Murtha | 502/168 |
| 4,409,410 | 10/1983 | Cosyns et al. | 585/259 |

Primary Examiner—D. E. Gantz
Assistant Examiner—Cynthia A. Prezlock
Attorney, Agent, or Firm—William H. Page, II; John F. Spears, Jr.

[57] ABSTRACT

A process is disclosed for the production of linear olefinic hydrocarbons. A feed stream of paraffins is fed to a catalytic dehydrogenation reaction zone. Liquid phase hydrocarbons withdrawn from the dehydrogenation reaction zone are passed through a diolefin selective hydrogenation zone. The effluent of the hydrogenation zone is stripped of light ends and passed into an olefin separation zone, which preferably employs a selective adsorbent. The paraffinic effluent of the separation zone is recycled to the dehydrogenation zone. The paraffinic recycle stream contains some monoolefins, but is essentially free of diolefins. Dehydrogenation catalyst life is lengthened by elimination of diolefins in total charge to dehydrogenation zone. Product quality and yield is improved.

9 Claims, 1 Drawing Figure

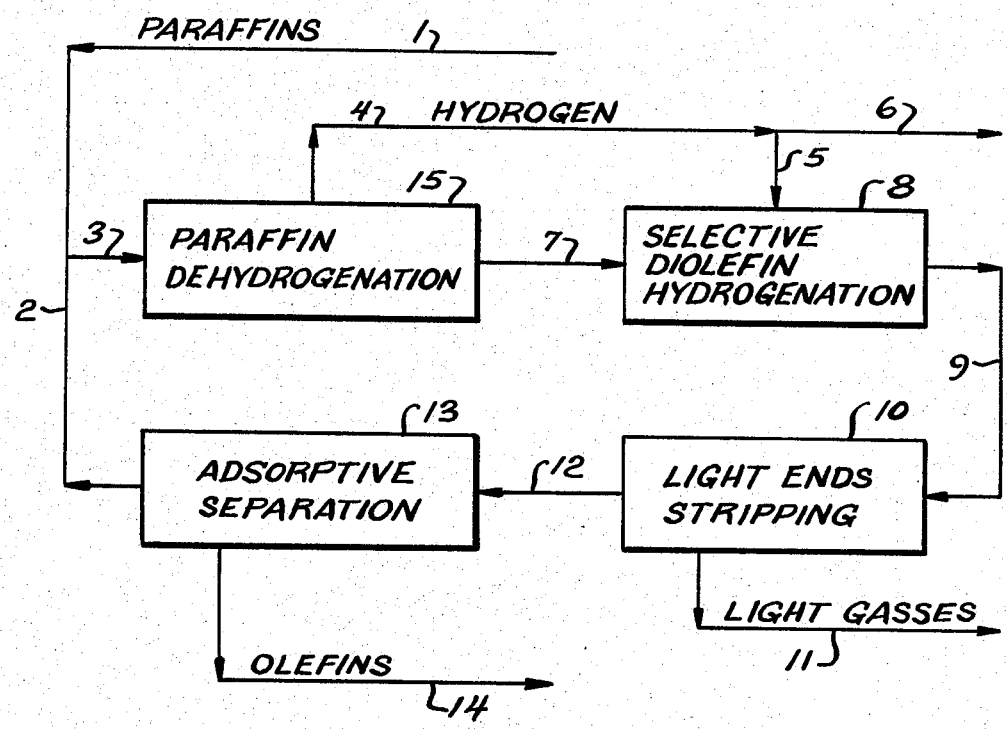

PROCESS FOR CONVERTING PARAFFINS TO OLEFINS

CROSS REFERENCE TO RELATED APPLICATION

This application is a continuation-in-part of my prior application Ser. No. 596,867 filed Apr. 4, 1984 entitled High Selectivity Process for Dehydrogenation of Paraffinic Hydrocarbons. The teaching of my prior application is incorporated herein.

FIELD OF THE INVENTION

The invention relates to the broad field of hydrocarbon processing. The invention may also be broadly classified as relating to a combination process for the production of olefinic hydrocarbons. More specifically, the invention relates to a hydrocarbon conversion process for the catalytic dehydrogenation of acyclic paraffinic hydrocarbons to produce monoolefinic hydrocarbons. The subject process also includes a selective hydrogenation step to eliminate diolefinic hydrocarbons, the adsorptive separation of olefins, and the recycling of unconverted paraffins. The selective hydrogenation converts diolefins present in the dehydrogenation reactor effluent stream to monoolefins.

INFORMATION DISCLOSURE

Processes for the dehydrogenation of acyclic hydrocarbons are well known to those skilled in the hydrocarbon conversion arts. Such processes are operated commercially in petroleum refineries and petrochemical plants. A representative process flow diagram of a dehydrogenation process is provided in an article appearing at pages 86–88 of the Jan. 26, 1970 issue of *Chemical Engineering*. The process is also described in U.S. Pat. No. 3,484,498 issued to R. C. Berg. The former reference illustrates the passage of a normal paraffin charge stream into a dehydrogenation reactor, with the effluent of this zone passing through a heat exchanger in which the vapor phase reactor effluent is partially condensed. The resultant mixed phase material is passed into a separating zone in which it is separated into a hydrogen-rich recycle stream and a liquid phase process stream. The liquid phase process stream is passed into a stripping column. Hydrocarbons which remain after stripping off the light hydrocarbons are passed into a downstream facility as the net product stream of the dehydrogenation zone.

U.S. Pat. No. 3,696,160 issued to K. D. Chomyn is pertinent for its teaching that those skilled in the art of hydrocarbon processing are aware that it may be beneficial to selectively hydrogenate diolefins to monoolefins in certain hydrocarbon streams. This reference is directed to the selective conversion of propadiene and butadiene contaminants in propylene and butene charge stocks employed in alkylation processes for the production of aviation and motor fuel. The reference indicates that supported nickel and palladium catalysts are excellent hydrogenation catalysts in the diolefin conversion service, but that their tendency to deactivate in sulfur-containing feedstocks limits their utilization. The reference discloses the use of a sulfided nickel-tungsten catalyst.

U.S. Pat. No. 3,655,621 issued to A. S. Kasperik et al illustrates a process for the selective hydrogenation of $C_4$ diolefins in an alkylation feed stream employing a catalyst comprising presulfided nickel supported on a refractory base. In U.S. Pat. No. 3,234,298 issued to W. C. van Zijll Langhout et al, a process is disclosed for the selective hydrogenation of light, diene-containing cracked hydrocarbon oils. This process is employed to increase the stability of such materials as pyrolysis gasoline and kerosene obtained by severe thermal cracking operations. The process is described as being applicable to diene-containing hydrocarbons ranging from $C_3$ to $C_{18}$ in carbon number. The process employs a catalyst comprising sulfided nickel on alumina or sulfided molybdenum on alumina.

U.S. Pat. No. 3,472,763 issued to J. Cosyns et al is pertinent for its description of a selective diolefin hydrogenation catalyst which comprises nickel supported on an alumina substrate having a number of specified characteristics and for its teaching of the utility of this catalyst. Specifically, it is taught that this catalyst may be employed for the conversion of all types of conjugated diolefins to monoolefins and in particular to the conversion of aliphatic conjugated diolefins having up to 15 carbon atoms per molecule to the corresponding monoolefins. As shown in U.S. Pat. No. 3,239,455 issued to A. G. Lickus et al, it is known to hydrotreat the feed stream to an adsorptive separation zone in which linear paraffins are separated from isoparaffins. The purpose of this is the elimination of sulfur-containing and nitrogen-containing compounds and olefinic compounds from the feed stream.

U.S. Pat. No. 3,617,504 issued to R. C. Berg is pertinent for its description of a combination process for producing linear monoolefins which employs a dehydrogenation zone and an adsorptive separation zone in a manner similar to that of the subject invention. The liquid phase hydrocarbons recovered from the dehydrogenation reactor are stripped of light ends and then passed into the separation zone. Olefins are recovered in this zone, leaving a paraffin-rich stream which is recycled to the dehydrogenation zone. U.S. Pat. No. 4,133,842 issued to M. C. Anderson is also highly pertinent as it describes a similar process for the production of linear monoolefins and includes a mild hydrotreating zone. The purpose of the mild hydrotreating zone is to saturate olefins present in the paraffin-rich recycle stream and a hydrogen-rich recycle gas stream fed to the dehydrogenation zone. It is stated that this saturation is intended to improve the quality of the desired monoolefinic product (col. 3, second paragraph). The reference also indicates that if this is not done, the charge to the dehydrogenation reactor will be "contaminated" and the reactor effluent will therefore contain non-linear olefins, aromatics, and diolefins (col. 2, lines 20-22). However, this reference hydrotreats the materials charged to the dehydrogenation reactor rather than a specific portion of the reactor effluent thus allowing impurities to be present in the ultimate product of the adsorptive separation zone. This is also indicative of a basic difference in the process. In the subject process, only diolefinic hydrocarbons are acted upon in the hydrogenation zone, and they are converted to monoolefins. The reference appears to describe the total saturation of all olefins. The advantages of the subject process are described below.

BRIEF SUMMARY OF THE INVENTION

The invention provides an improved process for the production of linear monoolefinic hydrocarbons from linear paraffinic hydrocarbons. The improved results are obtained through the use of a selective hydrogenation zone which converts diolefins present in the net product of the dehydrogenation zone to monoolefins. This increases the purity of the monoolefin product stream, increases dehydrogenation catalyst life, and decreases light by-product production.

One broad embodiment of the invention may be characterized as a process for the production of aliphatic monoolefinic hydrocarbons which comprises the steps of passing a feed stream, which comprises at least one $C_4$ to $C_{20}$ feed paraffins, and a hereinafter characterized recycle stream into a catalytic paraffin dehydrogenation zone maintained at dehydrogenation conditions and producing a dehydrogenation zone effluent stream, which comprises the feed paraffins and corresponding monoolefinic and diolefinic hydrocarbons; passing the dehydrogenation zone effluent stream through a selective catalytic hydrogenation zone at conditions effective to selectively convert diolefinic hydrocarbons to monoolefinic hydrocarbons; stripping hydrogen and light hydrocarbons from the dehydrogenation zone effluent stream; passing the dehydrogenation zone effluent stream into a separation zone in which olefinic hydrocarbons are concentrated into an olefin-rich product stream which is withdrawn, and also forming a separation zone effluent stream which is rich in the feed paraffins and which contains minor amounts of olefinic hydrocarbons; and passing at least a portion of the separation zone effluent stream into the dehydrogenation zone as the previously referred to recycle stream.

DESCRIPTION OF THE DRAWING

The drawing is a simplified flow diagram of a preferred embodiment of the invention. A feed stream comprising a mixture of $C_{10}$ to $C_{15}$ linear (straight chain) paraffins enters the process in line 1 and is admixed with a recycle stream from line 2, which comprises $C_{10}$ to $C_{15}$ paraffins and a minor amount of $C_{10}$ to $C_{15}$ monoolefins. The resultant reactor charge stream flows through line 3 into a paraffin dehydrogenation zone 15 wherein in the presence of a solid catalyst some of the paraffins are converted to monoolefins. Diolefins and light hydrocarbons are produced as by-products at a relatively small rate. A hydrogen-rich off gas stream comprising the net hydrogen of the reaction is vented off via lines 4 and 6. A liquid phase stream comprising condensed $C_{10}$-plus hydrocarbons, of which about 15 mole percent are olefins, and dissolved light hydrocarbons is passed through line 7 into a selective diolefin hydrogenation zone 8. Hydrogen from line 5 is added to ensure conversion of substantially all diolefins to monoolefins.

A hydrogenation zone effluent stream which is substantially free of diolefinic hydrocarbons is passed through line 9 into a light ends stripping zone 10 wherein such materials as hydrogen, methane, ethane, and in this case $C_9$-minus compounds are removed as the light gases removed in line 11. The remaining $C_{10}$ to $C_{15}$ paraffins and olefins pass through line 12 into an adsorptive separation zone 13 wherein over 90 mole percent of the olefins are concentrated into an olefin-rich product stream removed from the process in line 14. The remaining paraffins and olefins are recycled through line 2 as the recycle stream, which is sometimes referred to as the separation zone raffinate stream.

DETAILED DESCRIPTION

The production of acyclic olefinic hydrocarbons by dehydrogenation is a highly useful hydrocarbon conversion process. The product olefinic hydrocarbons find utility in the production of a wide variety of useful chemicals including synthetic lubricants, detergents, polymers, alcohols, plasticizers, etc. Modern catalytic dehydrogenation processes provide a high degree of selectivity. However, they are still troubled by the production of by-products, basically due to thermal cracking reactions and to undesired catalytic dehydrogenation side reactions. The by-products fall into two broad classes, light hydrocarbons formed by cracking reactions and diolefinic hydrocarbons having the same carbon number as the desired monoolefinic hydrocarbons. The production of diolefinic hydrocarbons is more troublesome, especially when the objective is to produce high purity monoolefinic hydrocarbons. The light byproducts which result from cracking reactions can normally be readily removed from the olefin-containing product stream by a relatively easy fractional distillation step. In comparison, diolefinic hydrocarbons are normally much more difficult to remove from a product stream since their physical characteristics such as volatility are very close to those of the product monoolefins. Furthermore, the presence of diolefins in an olefin product stream is often undesirable because the diolefins react in downstream processes to form different compounds than the monoolefins.

The presence of diolefinic hydrocarbons in an integrated process, such as the subject process in which a paraffin-rich material is recycled to the dehydrogenation zone, presents an additional problem. This problem is an increased rate of dehydrogenation catalyst deactivation compared to when feed boiling range hydrocarbons derived from the dehydrogenation reactor effluent are not returned to the dehydrogenation reactor. More specifically, the return of unsaturated hydrocarbons to the dehydrogenation zone inlet has been associated with catalyst lifes being reduced by 30 percent or more.

It is an objective of the subject invention to provide an improved process for converting linear paraffins to linear monoolefins. It is another objective of the invention to increase the life of dehydrogenation catalyst employed in an integrated dehydrogenation-separation process for the production of linear monoolefins. It is a further objective to reduce the production of by-products such as light ends and diolefinic hydrocarbons and to thereby increase the overall yield of monoolefins in such a process.

The subject invention is based on the selective hydrogenation of diolefins to monoolefins at a location between the dehydrogenation zone and the olefin separation zone. This process has a number of advantages over prior art processes including the previously cited U.S. Pat. No. 4,133,842. For instance, this reference process does not prevent diolefinic hydrocarbons from entering the separation zone. The olefin-rich product stream of the reference is therefore contaminated by a higher diolefin concentration than the product stream of the subject invention. A second disadvantage of the reference process is that monoolefins present in the recycle stream are saturated to paraffins in the hydrotreating zone. It is therefore necessary to redehydrogenate these same molecules in the dehydrogenation reactor. The number of passes through the relatively low conversion (15 mole percent) reaction zone to process the same number of molecules is thereby higher in the reference process. Since some light by-products are made during each pass through the dehydrogenation zone, the prior art process will produce more light ends from the same amount of feedstock at the same operating conditions. Furthermore, the presence of some olefins in the charge stream entering the reactor of the subject process reduces the amount of dehydrogenation required per pass to achieve the same olefin concentration in the hydrocarbon stream charged to the separation zone. The required operating conditions are, therefore, less severe in the subject process for equivalent space velocities through the reactor. The dehydrogenation reactor may be operated at a slightly lower temperature in the subject process if other parameters are equal. This reduces by-product formation by high temperature thermal cracking in heaters and in the reactor. Finally, it may also be observed that use of the selective hydrogenation at this particular location also increases the apparent yield of the process by converting by-product diolefins to desired monoolefins upstream of the separation zone.

It is also believed that selective hydrogenation will greatly reduce or eliminate the increased dehydrogenation catalyst deactivation observed when hydrocarbons are recycled from the separation zone. This is based on the concept that it is the presence of diolefinic hydrocarbons at the inlet of the catalyst bed which promotes coke deposition and catalyst deactivation. In a nonrecycle or olefin-free recycle dehydrogenation process, diolefinic hydrocarbons are rapidly removed from the catalyst bed due to the high space velocities normally employed in dehydrogenation reactors. Further, it is believed that it is necessary to first dehydrogenate a paraffin to a monoolefin before any diolefins are produced. The production of diolefins is, therefore, greatest at the near equilibrium conditions at the exit of a nonrecycle reactor, and most of the catalyst bed is accordingly spared severe deactivation by coke formation. Coke formation is believed to follow the production of polymeric or cyclic "coke precursors" which are derived from the diolefins. The rapid removal of diolefins from the reaction zone coupled with their formation in the later stages of the dehydrogenation reaction tends to minimize coke formation on the catalyst. In comparison the recycling of diolefins to the reactor tends to promote coke deposition and catalyst deactivation. The diolefins are then present in the entire catalyst bed and the whole bed is subjected to deactivation. The subject invention greatly reduces or eliminates the presence of diolefins in the charge stream of the reactor. It is believed this will be sufficient to significantly lengthen dehydrogenation catalyst life even though the charge stream still contains monoolefins.

The effect of the composition of a paraffinic recycle stream on the life of a dehydrogenation catalyst may be observed by a comparison of two common processes, both of which employ a dehydrogenation zone to produce linear olefins. In each case, a liquid phase stream containing the olefins and remaining paraffins is produced in the dehydrogenation zone. In a process flow in which this olefin-containing stream is passed into a reaction zone in which the monoolefins, and diolefins, are totally consumed and the remaining paraffins are recycled to the dehydrogenation zone, the preferred dehydrogenation catalyst would be expected to process about 220 barrels of paraffins before it is necessary to replace or regenerate the catalyst. An example of this process is the production of alkylbenzenes by the HF-catalyzed alkylation of benzene as described in U.S. Pat. Nos. 3,484,498; 3,494,971; 3,950,448; and 4,225,737. The HF is a very effective catalyst. All of the olefinic compounds not consumed in the alkylation reaction are consumed in oligomerization reactions. The paraffin recycle stream, therefore, is essentially free of all olefinic hydrocarbons. In comparison, the recycle stream from an absorptive separation in a process similar to that shown in previously referred to U.S. Pat. No. 3,617,504 will contain olefins and diolefins. Table VI of this reference gives specific amounts of paraffins, olefins, and diolefins in the recycle stream to the dehydrogenation zone. In a process such as this, it would be expected that the dehydrogenation catalyst would process about 150 barrels of paraffins per pound of catalyst before it is necessary to replace the catalyst. This is based on the same reactor conditions and same feedstock as the previously given catalyst life. It may thus be seen that rather severe premature catalyst deactivation occurs in the latter case due to the presence of the various olefinic hydrocarbons in the recycle stream. As previously described it is believed that the majority of this increased deactivation is caused by the presence of diolefins in the recycle stream.

The feed hydrocarbon charged to the subject process is a $C_4$-plus normal paraffin. Paraffins which contain six or more carbon atoms per molecule are preferred over $C_4$ and $C_5$ paraffins. The upper limit on the carbon number of the charge stock is basically set by the volatility and processability of the charge stock in the dehydrogenation reactor. This upper limit is at about $C_{22}$ paraffins. The feed stream may be a high purity stream of a single paraffin or the feed stream may comprise a mixture of two or more paraffins having different carbon numbers. For instance, an admixture of $C_{10}$ to $C_{15}$ normal paraffins is often passed through a dehydrogenation zone to produce linear olefins which are consumed in the production of linear alkylbenzenes suitable for use in the production of biodegradable detergents. It is normally preferred that the feed stream contains a series of paraffins having a carbon number range of four or more. Adsorptive separation is highly suited to processing such mixtures.

Conventional equipment and process flows can be used in the dehydrogenation zone. In this arrangement, a fresh paraffinic hydrocarbon feed stream and the recycle paraffin stream are combined with recycled hydrogen. This forms a reactant stream which is heated by indirect heat exchange and is then passed through a bed of a suitable catalyst maintained at the proper dehydrogenation conditions of temperture, pressure, etc. The effluent of this catalyst bed or reactor effluent stream is cooled and partially condensed and passed into a vapor-liquid separation zone. Part of the uncondensed material is employed as the hydrogen-rich recycle gas stream. The remainder of the uncondensed hydrogen-rich material is the net production of hydrogen which may be used in other applications such as desulfurization. As used herein, the term "rich" is intended to indicate a molar concentration of the indicated compound or class of compounds above 50%. The vapor-liquid separation zone also produces a liquid stream. This stream is basically an admixture of dehydrogenated and undehydrogenated acyclic hydrocarbons including diolefinic hydrocarbons. The dehydrogenated hydrocarbons have the same carbon numbers as the corresponding feed hydrocarbons. This liquid phase stream will also contain some dissolved hydrogen and light hydrocarbons produced by various cracking reactions which occur at the high temperatures employed in the dehydrogenation reactor and heaters.

In the subject process, the liquid phase process stream withdrawn from this separation zone is passed into a selective hydrogenation reaction zone. This reaction zone contains a selective hydrogenation catalyst and is maintained at conditions necessary for selective hydrogenation of diolefins to monoolefins. The placement of the selective hydrogenation zone at this point makes it very economical to perform the desired selective hydrogenation. One reason for this is that the reactants are in the desired liquid phase state as they leave the vapor-liquid separation zone. A second reason is that the temperature of the liquid phase process stream as it leaves the separation zone will normally be within the desired operating range of the selective hydrogenation reaction zone.

This location for the hydrogenation zone is also preferred since it allows the effluent of the hydrogenation zone to be stripped of hydrogen in the same stripping column required for the removal of light ends from the liquid phase stream condensed out of the dehydrogenation reactor effluent. This stripping column is usually desired in a selective hydrogenation process to ensure that hydrogen does not enter downstream processing units. For instance, it is normally undesirable to admit hydrogen and light ends into an absorptive separation zone or into a liquid-liquid extraction type separation zone. For instance, the light hydrocarbons may generate undesirable vapor loads in fractionation systems or accumulate in solvent and desorbent hydrocarbon streams thus diluting these materials. A separate but less important advantage to this process flow is that it allows at least partial utilization of the hydrogen dissolved in the liquid phase process stream in the hydrogenation step. This reduces the required rate of external hydrogen addition to the hydrogenation reactor. It thereby also increases the percentage of produced hydrogen which is available in the hydrogen-rich separator gas for removal from the process as a product stream. That is, the subject process flow at least partially consumes the dissolved hydrogen in the hydrogenation reaction rather than venting the hydrogen as a low concentration component of a hydrocarbon-rich stripper overhead vapor.

The selective hydrogenation conditions employed in the hydrogenation zone are preferably similar to that maintained in the vapor-liquid separation zone of the dehydrogenation process. More specifically, the minimum pressure should be sufficient to maintain the reactants as liquid phase hydrocarbons. A broad range of suitable operating pressures therefore extends from about 40 to about 1000 psig, with a pressure between about 50 and 300 psig being preferred. A relatively moderate temperature between about 25° and 350° C. is preferred. More preferably, the hydrogenation zone is maintained at a temperature between about 50° and about 200° C. The liquid hourly space velocity of the reactants through the selective hydrogenation zone should be above 1.0. Preferably, it is above 5.0 and more preferably it is between 5.0 and 35.0 hr.$^{-1}$. The optimum set of conditions will of course vary depending on such factors as the composition of the feed stream and the activity and stability of the hydrogenation catalyst.

Another variable operating condition is the ratio of hydrogen to diolefinic hydrocarbons maintained within the selective hydrogenation zone. The amount of hydrogen required to achieve a certain conversion is believed dependent upon reactor temperature and the molecular weight of the feed hydrocarbons. Also, some catalysts, such as a palladium on alumina catalyst which was tested, require a higher hydrogen concentration to achieve the desired degree of hydrogenation. Therefore, with some catalysts, such as the palladium catalysts, it may be desired to operate with a hydrogen to diolefinic hydrocarbon mole ratio of between 2:1 and 5:1. With this catalyst, it was determined that hydrogen concentrations above this range resulted in the saturation of a significant amount of monoolefinic hydrocarbons. This of course is undersirable as it reduces the yield of the process. With the preferred feedstock and the preferred nickel sulfide catalyst, there should be less than 2.0 times the stoichiometric amount of hydrogen required for the selective hydrogenation of the diolefinic hydrocarbons which are present in the liquid phase process stream to monoolefinic hydrocarbons. Preferably, the mole ratio of hydrogen to diolefinic hydrocarbons in the material entering the selective hydrogenation zone is maintained between 1:1 and 1.8:1. In some instances, it may be desirable to operate with a less than stoichiometrically required amount of hydrogen, with mole ratios down to 0.75:1 being acceptable.

The selective hydrogenation zone preferably comprises a single fixed bed reactor containing a cylindrical bed of catalyst through which the reactants move in a vertical direction. It is preferred that the reactants flow upward through the reactor as this provides good mixing. The catalyst may be present at pellets, spheres, extrudates, irregular shaped granules, etc. The prior art suggests the use of a number of metals on selective hydrogenation catalysts including tungsten, palladium, silver, molybdenum, and nickel. Of these metals, it is preferred that the active catalytic metal component present in the hydrogenation catalyst is either nickel or palladium, with nickel being especially preferred. When non-noble metals are employed, the catalyst should have a high concentration or loading of the active metal, with the metal component preferably comprising over 5 wt.% of the catalytic composite. More preferably, over 10 wt.% of the catalytic composite is metallic. It is very highly preferred that the selective hydrogenation catalyst also comprises a sulfur component. The preferred catalyst may therefore be described as a sulfided high nickel catalyst. The preparation of catalysts of the desired nature is described in U.S. Pat. No. 3,919,341. The preferred selective hydrogenation catalyst has a lower sulfur concentration than the catalyst described in this reference, with sulfur levels between about 0.1 and 0.4 wt.% being preferred. The basic function of the sulfur component is believed to be the attenuation of the hydrogenation activity of the nickel. It is known in the art that carbon monoxide may be passed into a selective hydrogenation reactor for the purpose of moderating or attenuating the hydrogenation reaction. Carbon monoxide and other such moderators may be employed though not necessary or desired in the subject process.

The selective hydrogenation catalyst also comprises a support or carrier material which should be relatively inert and refractory to the conditions employed within the process. The support can be formed from a variety of porous materials including various clays, diatomaceous earth, aluminas, ceramics, attapulgus clay, and other synthetically prepared or naturally occurring silicates, kaolin, kieselguhr, titania, alumina, crystalline aluminosilicates, and admixtures of two or more of these materials. The especially preferred carrier material is an alumina. Of the aluminas, gamma-alumina is preferred. The carrier material or support may have an apparent bulk density of about 0.3 to about 0.8 g/cc, a surface area of about 50 to about 550 m$^2$/g, and a pore volume of between about 0.1 and about 1.0 ml/g.

The effluent of the selective hydrogenation zone is a liquid phase stream similar in nature to the liquid phase process stream removed from the separator of the dehydrogenation zone but having a reduced concentration of diolefinic hydrocarbons and a corresponding increase in the concentration of monoolefinic hydrocarbons. This effluent stream is passed into a stripping column designed and operated to remove overhead all compounds which are more volatile than the lightest hydrocarbon which it is desired to have present in the net effluent stream of the dehydrogenation process. These lighter materials will be concentrated into a net overhead stream which will comprise an admixture of hydrogen and light hydrocarbons. The purpose of the stripping operation is to prevent the entrance of volatile light materials into downstream processing zones where they could present certain operational problems. The stripping column also serves to eliminate the light hydrocarbons from the recycle stream which returns paraffinic hydrocarbons to the dehydrogenation zone from the downstream separation zone. The recycling of light hydrocarbons to the dehydrogenation zone is not desired as it normally has an adverse impact on the dehyrogenation catalyst. The stripping column can also be operated to adjust the initial boiling point or composition of the effluent of the downstream adsorptive separation zone.

The dehydrogenation zone employed in the process will contain a reaction zone and associated auxiliary process equipment such as condensers and a vapor-liquid separator which receives the partially condensed reactor effluent stream. The preferred configuration of this zone is described above. The dehydrogenation reaction zone preferably comprises at least one radial flow reactor in which the catalyst gradually moves downward by gravity flow to allow the continuous replacement of used catalyst with catalyst having a higher activity. It is preferred that the reactants make at least two passes through a catalyst bed within the reaction zone. A detailed description of moving bed reactors of this type may be obtained by reference to U.S. Pat. Nos. 3,647,680; 3,706,536; 3,825,116; 3,839,196; 3,839,197; 3,854,887; 3,856,662; and 3,978,150.

The particular dehydrogenation conditions employed within the reaction zone may vary depending on such factors as the catalyst activity, feed carbon number, and the desired conversion. The reaction zone conditions normally employed for C$_6$-plus paraffin dehydrogenation include a temperature of from about 400° to 600° C., a pressure of from 0.5 to about 10 atmospheres, and a liquid hourly space velocity of about 1 to 20. The preferred operating temperature for C$_{10}$ to C$_{15}$ paraffins is within the range of from about 450° to 550° C., and the preferred operating pressure is about 0.5 to 2 atmospheres.

The composition of the dehydrogenation catalyst is not believed to materially affect the operation of the subject process provided this catalyst meets commercial standards for activity, stability, and selectivity. Dehydrogenation catalysts are described in U.S. Pat. Nos. 3,274,287; 3,315,007; 3,315,008; 3,745,112; and 4,430,517. These catalysts comprise a platinum group component supported on a porous carrier material. The preferred carrier material is a refractory inorganic oxide such as gamma-alumina. The preferred dehydrogenation catalysts contain on an elemental basis 0.01 to 2 wt.% platinum group component and about 0.1 to 5 wt.% of an alkali or alkaline earth metal. Preferably, there is present 0.05 to 1 wt.% platinum group component and about 0.25 to 3.5 wt.% of the alkali or alkaline earth component. The platinum group component may be chosen from the group consisting of platinum, palladium, rhodium, ruthenium, osmium, and iridium, but platinum is highly preferred. The alkali or alkaline earth component may be selected from the group consisting of the alkali metals—cesium, rubidium, potassium, sodium, and lithium; and the alkaline earth metals—calcium, strontium, barium, and magnesium. This component is preferably either lithium or potassium, with lithium being especially preferred. Another example of a suitable dehydrogenation catalyst is a catalyst which, in addition to the previously described platinum and alkali or akaline earth metal components, contains a tin component. This catalytic composite would contain from about 0.1 to about 1 wt.% tin. Yet another catalytic composite which should be highly suited for use in the subject process comprises an indium component in addition to the platinum, tin, and alkali or alkaline earth components. The indium component may be present on an elemental basis equal to about 0.1 to about 1 wt.% of the final composite. It is also known in the art that some catalytic composites of this nature may benefit from the presence of a small amount of a halogen component, with chlorine being the normally preferred halogen. Typical halogen concentrations in the final catalytic composite range from about 0.1 to about 1.5 wt.%. A halogen component is not desired in all situations. These catalytic composites are known to those skilled in the art and are described in the available references.

The type of separation zone used to recover the product olefins from the paraffin-olefin mixture is not a limiting characteristic of the subject process. Separatory techniques based upon liquid-liquid extraction or chemical binding can, therefore, be employed if they meet commercial standards of cost, effectiveness, and workability. It is greatly preferred that an absorptive type separation is employed, with the paraffin-olefin mixture being passed through a bed of a solid adsorbent which selectively collects either the olefins or the paraffins from the flowing stream. The selective retention of the olefins is preferred as there is a smaller quantity of olefins. This could be performed in a simple swing bed system with one or more beds being used to collect olefins while previously used beds are being regenerated as by the use of a desorbent, a temperature increase, a pressure decrease, or a combination of these commonly employed regeneration techniques. Another type of adsorptive separation process which may be employed is described in U.S. Pat. No. 4,402,832. This process simulates continuous cocurrent movement of the adsorbent relative to the fluid flow.

A preferred configuration of the adsorptive separation zone is described in U.S. Pat. Nos. 3,239,455; 3,617,504; and 4,133,842. The use of this separatory technique to separate olefinic hydrocarbons from a paraffin-olefin mixture is the subject of U.S. Pat. Nos. 3,510,423; 3,720,604; 3,723,302; and 3,755,153. These references describe operating conditions and methods and suitable adsorbents. They also describe in some detail the use of a preferred technique for simulating countercurrent flow of the feed hydrocarbons and the adsorbent. A variation in the equipment used to perform this process is the subject of U.S. Pat. No. 4,434,051. Adsorptive separations can be performed using either vapor phase or liquid phase conditions within the adsorption zone. The use of liquid phase methods is preferred as it allows operation at lower temperatures, which minimizes any polymerization of olefins. Operating conditions for the adsorbent chambers can include a temperature of from about 25° to about 225° C. and a pressure of from about atmospheric to 750 psig.

A sorptive separation step can be practiced using any type of commercially operable and practical selective adsorbent. The adsorbent may, therefore, be a naturally occurring substance or a man-made material and may be in the form of extrudates, pellets, spheres, etc. The adsorbent can be formed from charcoal, alumina, silica, or various clays, and mixtures of these materials. The preferred adsorbent comprise a selective zeolite commonly referred to as a molecular sieve. The preferred zeolites comprise synthetic crystalline aluminosilicates. Since the pure zeolites are relatively soft and powdery, the commercially used molecular sieves comprise a binder such as clay or alumina to produce a stronger and more attrition-resistant adsorbent particle. The adsorbent particles preferably have a size range of about 20 to about 40 mesh. The adsorbents which can be used in the process include the Type X or Type Y structured crystalline aluminosilicates or the naturally occurring faujasite species. The Type X zeolite is described in U.S. Pat. No. 2,882,244 while the Type Y zeolite is described in U.S. Pat. No. 3,130,007. The adsorbents as described above can contain cations selected from the group consisting of alkali metals (Group I-A), the alkali-earth metals (Group II-A), the coinage metals (Group I-B), or the Group II-B metals. Preferred metals selected from the aforementioned group include lithium, sodium, potassium, magnesium, calcium, strontium, barium, copper, silver, gold, zinc, cadmium, and mercury. Additionally, combinations of the above-mentioned metals may be included to enhance the adsorbent's selectivity for the olefins and to help reduce the harmful effects of side reactions including polymerization.

It is preferred to remove olefins from the adsorbent through the use of a liquid phase desorbent which is passed through the adsorbent bed. The desorbents which can be used in this process include olefinic-type hydrocarbons which boil at temperatures sufficiently different than the boiling temperature of the feedstock. Both branched chain or straight chain monoolefins can be used as desorbents. Additionally, aromatic-type hydrocarbons may be used as desorbents. In some instances, it will be advantageous to employ desorbents which contain a mixture of normal olefins or isoolefins and, normal or isoparaffins or paraffins or aromatics. Typical desorbents which can be used for a feedstock containing $C_{10}$ to $C_{14}$ monoolefins and paraffins is a desorbent mixture comprising about 80 volume percent octene-1 and 20 volume percent isooctane. In most instances, it is preferred to use a lower molecular weight desorbent mixture as compared to the feedstock. An example of a desorbent which can be used when $C_6$ to $C_9$ feedstock being separated is a desorbent containing about 80% of a straight chain butylene and about 20 volume percent of normal butane.

Most separation methods do not perform perfect separations. In large scale commercial processes, it often becomes prohibitively costly to perform a complete recovery or separation of hydrocarbons. This is also true in the case of absorptive recovery of olefins from the paraffin-olefin mixture. Recoveries of olefinic hydrocarbons can exceed 99 mole percent with the preferred simulated moving bed system, but the purity of the olefin product suffers as the recovery is increased. For this reason, most commercial process units are designed and operated to recover from 90 to about 95 mole percent of the olefins per pass. Therefore, about 5 to 10 mole percent of the original olefinic hydrocarbons will remain in the paraffinic recycle or raffinate stream which is passed into the dehydrogenation zone. This recycle stream will contain from about 0.4 to about 1.9 mole percent monoolefins in the subject process. This olefin concentration is significant due to its effects on the required operation of the dehydrogenation zone, as previously discussed, in comparison to processes which recycle an olefin-free hydrocarbon stream to the dehydrogenation zone.

A preferred embodiment of the invention may accordingly be characterized as a process for the production of $C_6$-plus linear monoolefins which comprises the steps of passing a feed stream comprising at least two $C_6$-plus feed paraffins and a hereinafter characterized recycle stream into a catalytic dehydrogenation zone operated at dehydrogenation conditions and producing a hydrogen-rich gas stream and a liquid phase dehydrogenation zone effluent stream which comprises dehydrogenation by-product light hydrocarbons, the two feed paraffins, and corresponding monoolefinic and diolefinic hydrocarbons; passing the dehydrogenation zone effluent stream through a catalytic selective hydrogenation zone operated at conditions effective to selectively convert diolefinic hydrocarbons to monoolefinic hydrocarbons without saturating monoolefinic hydrocarbons and thereby forming a hydrogenation zone effluent stream which comprises the dehydrogenation by-product light hydrocarbons, the two feed paraffins and corresponding monoolefinic hydrocarbons and which has a lower concentration of diolefinic hydrocarbons than the dehydrogenation zone effluent stream; removing dissolved hydrogen and by-product light hydrocarbons from the hydrogenation zone effluent stream in a fractionation zone; contacting the hydrogenation zone effluent stream with a solid adsorbent in an absorptive separation zone and separating the hydrogenation zone effluent stream into a product stream, which is rich in the olefinic hydrocarbons and is withdrawn from the process, and a separation zone effluent stream which is rich in the feed paraffins and which also contains minor amounts of olefinic hydrocarbons; and passing at least a portion of the separation zone effluent stream into the dehydrogenation zone as the previously referred to recycle stream. This recycle stream is preferably passed directly into the dehydrogenation zone as shown in the drawing. However, it must be realized that in commercial scale operations process streams may be routed through storage facilities which serve to buffer flow rate differences between different process units. The recycle stream and other streams may therefore flow through tankage or surge drums within the integrated process. Other fractionation steps can also be employed within the overall process to remove undesired compounds, etc.

I claim as my invention:

1. A process for the production of substantially diolefin-free monoolefinic hydrocarbons which comprises:

(a) passing a feed stream comprising at least one $C_4$ to $C_{20}$ feed paraffinic hydrocarbon and a hereinafter derived recycle stream characterized as having a monoolefin hydrocarbon concentration of between 0.4 and 1.9 mole percent into a catalytic paraffin dehydrogenation zone maintained at dehydrogenation conditions containing a dehydrogenation catalyst to produce a dehydrogenation zone effluent stream comprising light hydrocarbons, hydrogen, feed paraffinic hydrocarbons and corresponding monoolefinic and diolefinic hydrocarbons;

(b) passing at least a portion of said dehydrogenation zone effluent stream through a selective catalytic hydrogenation zone containing a selective hydrogenation catalyst in the presence of hydrogen having a ratio of 1:1 to 1.8:1 of hydrogen to said diolefinic hydrocarbons and at conditions selected to convert nearly all said diolefinic hydrocarbons to monoolefinic hydrocarbons and to produce a hydrogenation zone effluent stream substantially free of diolefins and containing relatively the same content of paraffinic hydrocarbons as contained in said dehydrogenation zone effluent stream;

(c) passing said hydrogenation effluent stream to a stripping zone to strip hydrogen and light hydrocarbons from said hydrogenation zone effluent stream;

(d) passing said stripped hydrogenation stream to a separation zone effective to concentrate said monoolefinic hydrocarbons into a substantially diolefin-free monoolefinic hydrocarbon-rich product stream and effective to produce a paraffinic hydrocarbon-rich separation zone effluent stream having a monoolefinic hydrocarbon concentration of between 0.4 and 1.9 mole percent; and (e) passing at least a portion of said paraffinic hydrocarbon-rich separation zone effluent stream into said dehydrogenation zone of step (a) as said characterized recycle stream.

2. The process of claim 1 further characterized in that the feed stream comprises feed paraffins having two different carbon numbers.

3. The process of claim 1 further characterized in that the feed stream comprises feed paraffins having three different carbon numbers.

4. The process of claim 3 further characterized in that the dehydrogenation zone effluent stream is a liquid phase stream.

5. The process of claim 4 further characterized in that the separation zone comprises a fixed bed of a solid adsorbent which selectively adsorbs either olefinic or paraffinic hydrocarbons.

6. The process of claim 5 further characterized in that all of the separation zone effluent stream is passed into the dehydrogenation zone.

7. A process for the production of substantially diolefin-free $C_6$-plus linear monoolefins which comprises the steps of:

(a) passing a feed stream comprising at least two $C_6$-plus feed paraffinic hydrocarbons and a recycle stream characterized as having a monoolefin content of between 0.4 and 1.9 mole percent monoolefinic hydrocarbons into a catalytic dehydrogenation zone containing a dehydrogenation catalyst operated at dehydrogenation conditions to produce a hydrogen-rich gas stream and a liquid phase dehydrogenation zone effluent stream which comprises dehydrogenation by-product light hydrocarbons, said two feed paraffinic hydrocarbons, and corresponding monoolefinic and diolefinic hydrocarbons;

(b) passing said dehydrogenation zone effluent stream through a catalytic selective hydrogenation zone containing hydrogenation catalyst operated at conditions effective to selectively convert said diolefinic hydrocarbons to monoolefinic hydrocarbons without saturating said monoolefinic hydrocarbons and forming a hydrogenation zone effluent stream which comprises the dehydrogenation by-product light hydrocarbons, the two feed paraffinic hydrocarbons and corresponding monoolefinic hydrocarbons and which has a lower concentration of diolefinic hydrocarbons than the dehydrogenation zone effluent stream;

(c) passing said hydrogenation effluent stream to a fractionation zone to remove dissolved hydrogen and by-product light hydrocarbons from said hydrogenation zone effluent stream;

(d) contacting the hydrogenation zone effluent stream with a solid adsorbent in an absorptive separation zone and separating the hydrogenation zone effluent stream into said substantially diolefin-free product stream, which is rich in the monoolefinic hydrocarbons and is withdrawn from the process, and a separation zone effluent stream which is rich in the feed paraffinic hydrocarbons and which contains between 0.4 to 1.9 mole percent monoolefinic hydrocarbons; and, (e) passing at least a portion of the separation zone effluent stream into said dehydrogenation zone of step (a) as the previously characterized recycle stream.

8. The process of claim 7 further characterized in that the feed stream comprises $C_{10}$ to $C_{15}$ paraffins.

9. The process of claim 7 further characterized in that a catalyst comprising sulfided nickel and alumina is employed within the selective hydrogenation zone.

* * * * *